(12) United States Patent
Feng

(10) Patent No.: US 10,182,759 B2
(45) Date of Patent: Jan. 22, 2019

(54) SELF-CHARGING ELECTRONIC BRACELET

(71) Applicants: Fu Tai Hua Industry (Shenzhen) Co., Ltd., Shenzhen (CN); HON HAI PRECISION INDUSTRY CO., LTD., New Taipei (TW)

(72) Inventor: Yu-Zhong Feng, Shenzhen (CN)

(73) Assignees: Fu Tai Hua Industry (Shenzhen) Co., Ltd., Shenzhen (CN); HON HAI PRECISION INDUSTRY CO., LTD., New Taipei (TW)

( * ) Notice: Subject to any disclaimer, the term of this patent is extended or adjusted under 35 U.S.C. 154(b) by 0 days.

(21) Appl. No.: 15/814,715

(22) Filed: Nov. 16, 2017

(65) Prior Publication Data

US 2018/0310882 A1 Nov. 1, 2018

(30) Foreign Application Priority Data

Apr. 28, 2017 (CN) .......................... 2017 1 0296808

(51) Int. Cl.
*H05K 7/00* (2006.01)
*A61B 5/00* (2006.01)
*A44C 5/00* (2006.01)
*H05K 1/18* (2006.01)
*H01F 7/02* (2006.01)

(52) U.S. Cl.
CPC .......... *A61B 5/6802* (2013.01); *A44C 5/0007* (2013.01); *H01F 7/02* (2013.01); *H05K 1/189* (2013.01)

(58) Field of Classification Search
CPC ....................................................... H02K 7/18
USPC ..................................................... 361/679.01
See application file for complete search history.

(56) References Cited

U.S. PATENT DOCUMENTS

2015/0311741 A1* 10/2015 Baker .................. H02J 7/0044
320/108
2016/0336836 A1* 11/2016 Bickers ................. H02K 21/24

* cited by examiner

*Primary Examiner* — Jerry Wu
(74) *Attorney, Agent, or Firm* — ScienBiziP, P.C.

(57) ABSTRACT

An electronic bracelet includes a wristband including a first layer and a second layer. The second layer is rotatable relative to the first layer. One of the first layer and the second layer includes a number of permanent magnets. The other of the first layer and the second layer includes a number of coils. A control module is fixed on the wristband. The second layer rotates relative to the first layer to generate electricity for the control module.

16 Claims, 6 Drawing Sheets

SELF-CHARGING ELECTRONIC BRACELET

CROSS-REFERENCE TO RELATED APPLICATIONS

This application claims priority to Chinese Patent Application No. 201710296808.2 filed on Apr. 28, 2017, the contents of which are incorporated by reference herein.

FIELD

The subject matter herein generally relates to electronic bracelets, and more particularly to a self-charging electronic bracelet.

BACKGROUND

Electronic bracelets are widely used for collecting personal data such as health data when doing exercise.

BRIEF DESCRIPTION OF THE DRAWINGS

Implementations of the present disclosure will now be described, by way of example only, with reference to the attached figures.

DETAILED DESCRIPTION

Figure 1:
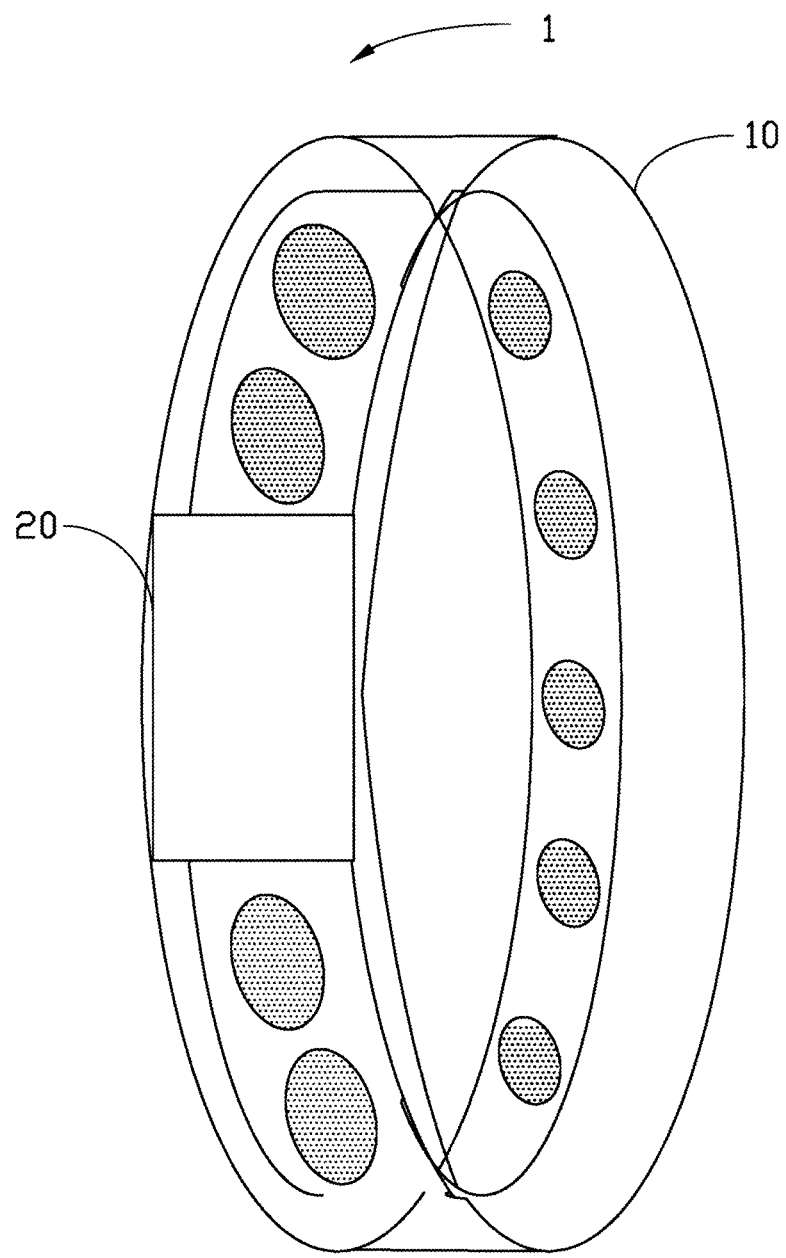
FIG. 1 is a diagram of an exemplary embodiment of an electronic wristband.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape, or other word that "substantially" modifies, such that the component need not be exact. For example, "substantially cylindrical" means that the object resembles a cylinder, but can have one or more deviations from a true cylinder. The term "comprising" means "including, but not necessarily limited to"; it specifically indicates open-ended inclusion or membership in a so-described combination, group, series and the like.

FIG. 1 illustrates an exemplary embodiment of an electronic bracelet 1. The electronic bracelet 1 can include, but is not limited to, a wristband 10 and a control module 20. The control module 20 can be fixed on the wristband 10.

Figure 2:
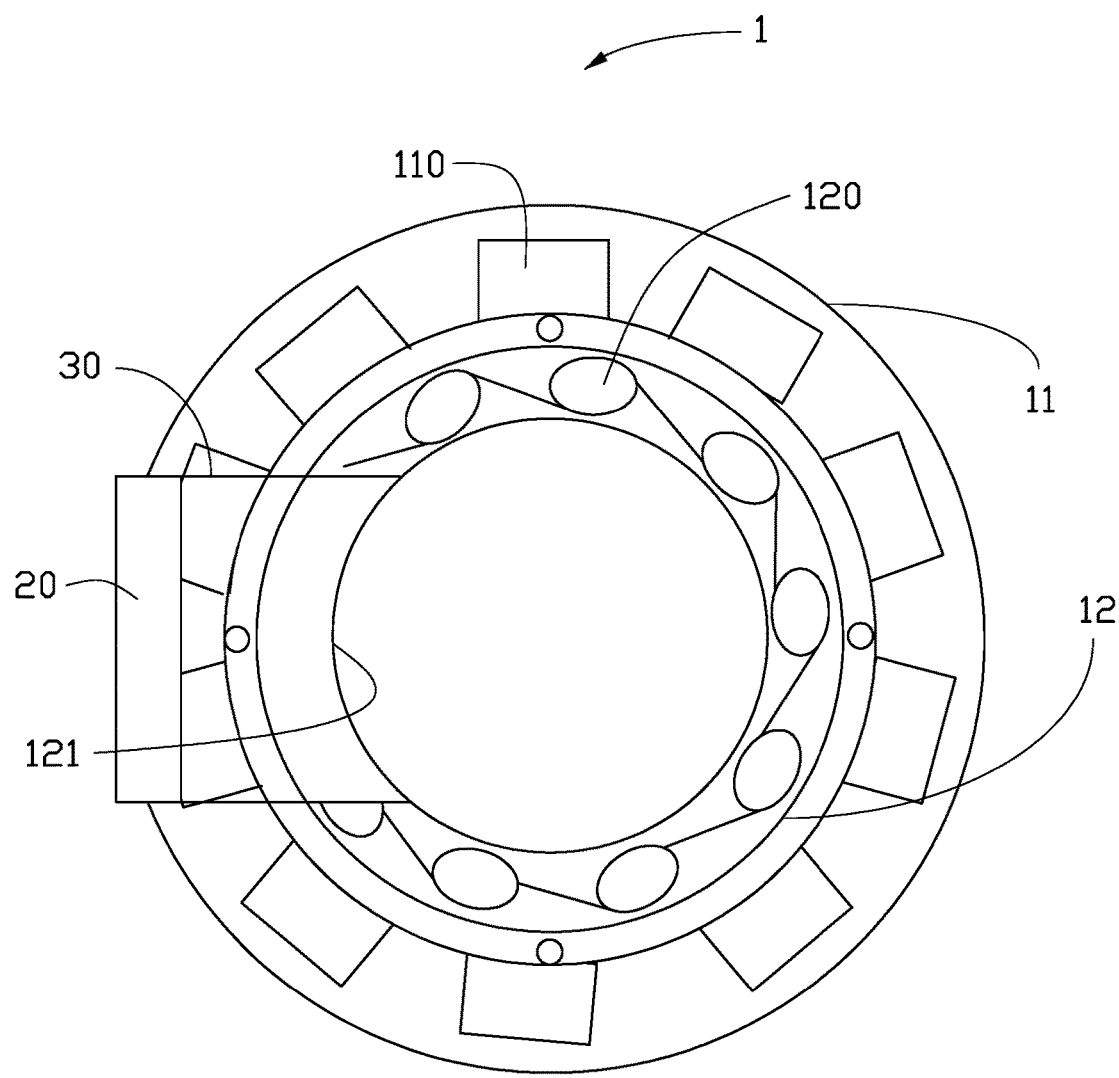
FIG. 2 is a diagram of the electronic wristband.

Referring to FIG. 2, the wristband 10 can include a first layer 11 and a second layer 12. In at least one embodiment, the first layer 11 covers over the second layer 12. The first layer 11 can include a plurality of permanent magnets 110, and the second layer 12 can include a plurality of coils 120. The control module 20 can be electrically coupled to the second layer 12. When the wristband 10 is worn by a user, the second layer 12 can rotate relative to the first layer 11 through exercise or daily motion of the user to generate electricity for the control module 20.

Figure 3:
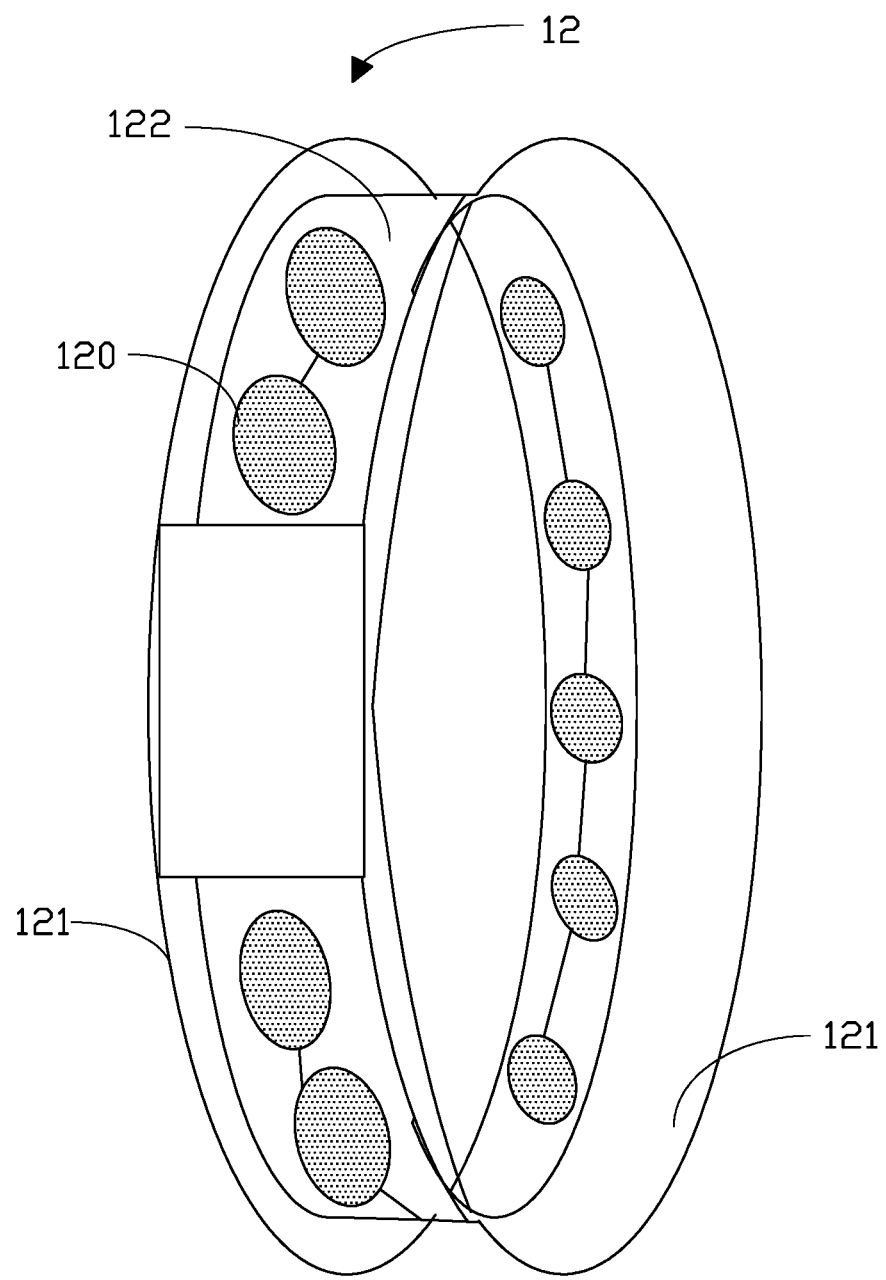
FIG. 3 is similar to FIG. 1.

Referring to FIG. 3, the second layer 12 can include a side ridge 121 formed on opposite sides of the second layer 121. The side ridges 121 can extend toward the first layer 11, and a sliding groove 122 can be defined between the side ridges 121. The plurality of coils 120 can be received within the sliding groove 122. In at least one embodiment, the coils 120 can be flexible printed circuit boards. The coils 120 can be circular, oval, or quadrilateral shaped. The coils 120 can be electrically coupled to each other in series or in parallel.

Figure 4:
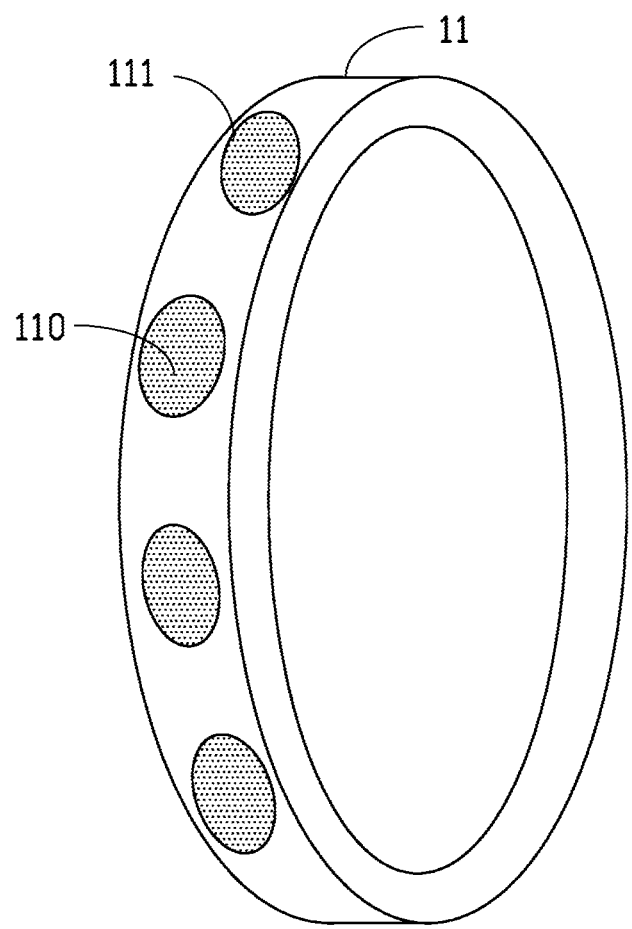
FIG. 4 is a diagram of a first layer of the wristband of FIG. 1.

Referring to FIGS. 1 and 4, in at least one embodiment, the first layer 11 covers over the sliding groove 122. The first layer 11 can be substantially hollow. A surface within the first layer 11 can define a plurality of holding grooves 111. Each of the holding grooves 111 can receive a corresponding one of the permanent magnets 110.

Figure 5:
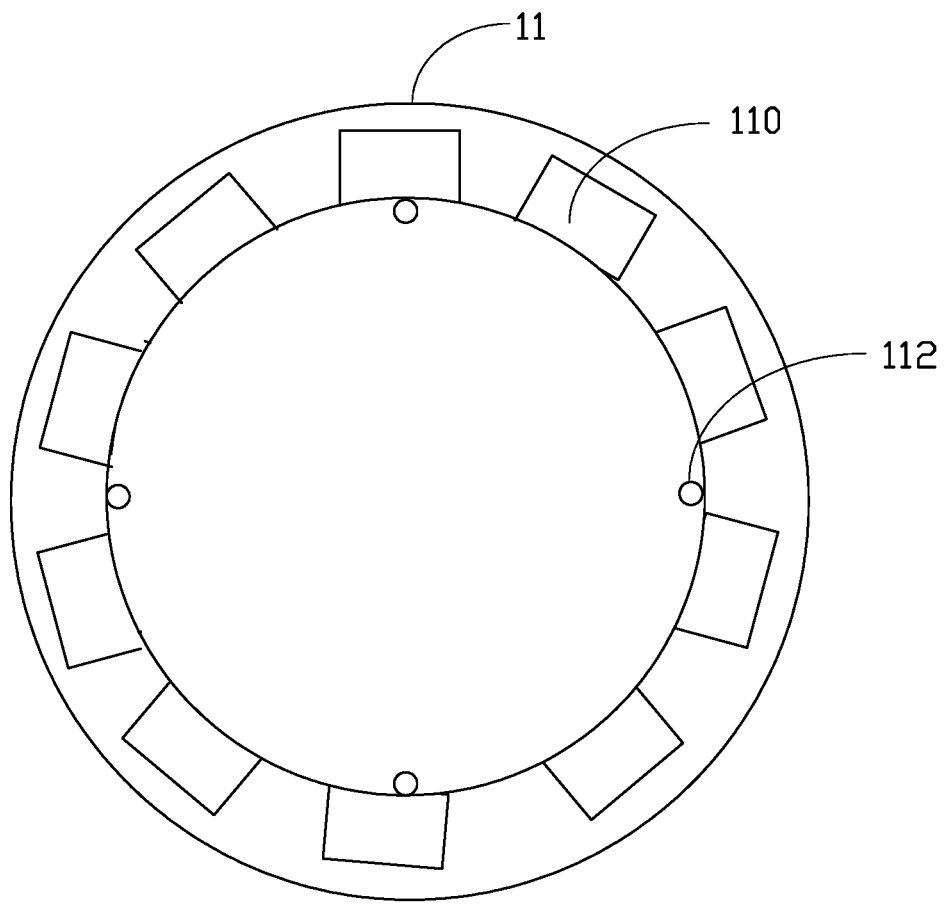
FIG. 5 is a side view of FIG. 4.

Referring to FIG. 5, the first layer 11 can further include a plurality of protrusions 112. The protrusions 112 can be on a surface of the first layer 11 adjacent to the second layer 12. The protrusions 112 can be received within the receiving groove 122 and are made of glass or other low-friction material. The protrusions 112 can reduce friction between the first layer 11 and the second layer 12 when the second layer 12 is rotated relative to the first layer 11.

Referring again to FIG. 2, the electronic bracelet 1 can further include a frame 30 fixed to the side ridges 121 of the second layer 12. The control module 20 can be arranged on the frame 30. The frame 30 and the side ridges 121 can include circuitry (not shown) electrically coupled between the control module 20 and the plurality of coils 120. Thus, the control module 20 can be electrically coupled to the plurality of coils 120 through the circuitry of the frame 30 and the side ridges 121.

Figure 6:
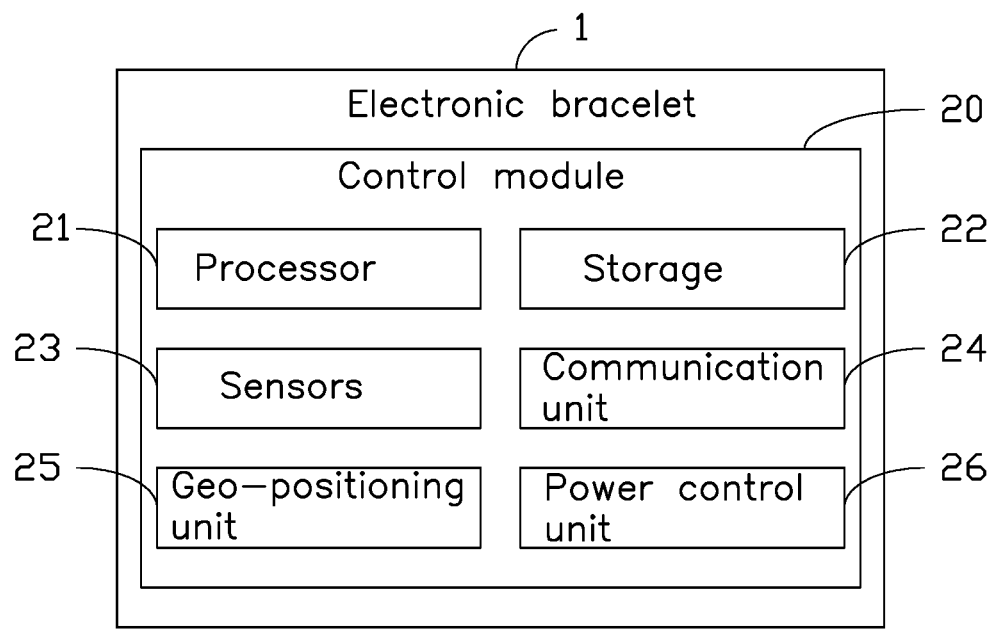
FIG. 6 is a diagram showing modules of a control module of the electronic wristband in FIG. 1.

Referring to FIG. 6, the control module 20 can include, but is not limited to, a processor 21, a storage 22, a plurality of sensors 23, a communication unit 24, a geo-positioning unit 25, and a power control unit 26. The control module 20 can carry out a variety of functions, such as recording, uploading, and synchronizing user health data, for example. The power control unit 26 can store electricity generated by the plurality of coils 120 and provide electricity for use by the control module 20. The processor 21 can be a microprocessing chip. The storage 22 can be a memory chip. The communication unit 24 can be a BLUETOOTH module or a WIFI module. The geo-positioning unit 25 can be a GPS (Global Positioning System).

When the electronic bracelet 1 is worn on the hand of a user, the first layer 11 can passively rotate relative to the second layer 12 by movement of the user. When electric power of the electronic bracelet 1 is not sufficient, the user can manually rotate the first layer 11 relative to the second layer 12 to generate electricity. In at least one embodiment, the plurality of coils 120 can generate electricity according to Faraday's law of electromagnetic induction. The power control unit 26 can store the electricity generated by the plurality of coils 120 and provide the electricity for use by the control module 20.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. An electronic bracelet comprising: a wristband comprising a first layer and a second layer, the first layer covering the second layer, the second layer rotatable relative to the first layer, one of the first layer and the second layer comprising a plurality of permanent magnets, the other of the first layer and the second layer comprising a plurality of coils; a control module fixed on the wristband and electrically coupled to the second layer, the first layer rotating around the second layer while the second layer remains stationary to generate electricity for the control module, and a frame fixed to the second layer, wherein two side ridges are formed on opposite sides of the second layer respectively, the side ridges extend toward the first layer, a sliding groove is defined between the side ridges, and the frame is fixed to the side ridges, wherein the control module is arranged on the frame, wherein the control module is electrically coupled to the second layer through the frame and the side ridges.

2. The electronic bracelet of claim 1, wherein the plurality of permanent magnets is in the first layer, the plurality of coils is in the second layer.

3. The electronic bracelet of claim 2, wherein the first layer is hollow, a surface within the first layer defines a plurality of holding grooves, each of the holding grooves receives one of the plurality of permanent magnets.

4. The electronic bracelet of claim 3, wherein the first layer comprises a plurality of protrusions, the protrusions are on a surface of the first layer adjacent to the second layer.

5. The electronic bracelet of claim 4, wherein the frame and the side ridges comprise circuitry electrically coupled between the control module and the plurality of coils; wherein the control module is electrically coupled to the plurality of coils through the circuitry of the frame and the side ridges.

6. The electronic bracelet of claim 5, wherein the control module stores electricity generated by the plurality of coils.

7. The electronic bracelet of claim 1, wherein a shape of the holding grooves matches a shape of the permanent magnets.

8. The electronic bracelet of claim 1, wherein a shape of the plurality of coils and a shape of the plurality of permanent magnets are circular.

9. The electronic bracelet of claim 1, wherein a shape of the plurality of coils and a shape of the plurality of permanent magnets are oval.

10. The electronic bracelet of claim 1, wherein a shape of the plurality of coils and a shape of the plurality of permanent magnets are quadrilateral.

11. The electronic bracelet of claim 1, wherein the plurality of coils is electrically coupled in parallel.

12. The electronic bracelet of claim 1, wherein the plurality of coils is electrically coupled in series.

13. The electronic bracelet of claim 1, wherein the plurality of permanent magnets is circular.

14. The electronic bracelet of claim 1, wherein the plurality of permanent magnets is oval.

15. The electronic bracelet of claim 1, wherein the plurality of permanent magnets is quadrilateral.

16. The electronic bracelet of claim 1, wherein the plurality of coils is flexible printed circuit boards.

* * * * *